United States Patent [19]

Hangartner et al.

[11] 4,011,335

[45] Mar. 8, 1977

[54] METHYLENE DIOXYPHENYL ETHERS

[75] Inventors: Walter Hangartner, Schofflisdorf; René Zurflueh, Pfaffhausen, both of Switzerland

[73] Assignee: Hoffmann-La Roche Inc., Nutley, N.J.

[22] Filed: June 5, 1975

[21] Appl. No.: 584,246

[30] Foreign Application Priority Data

June 17, 1974 Switzerland .............. 8250/74

[52] U.S. Cl. .............. 424/282; 260/340.5; 260/456 P; 260/586 G; 260/638 B; 260/638 G; 260/654 R; 426/321; 426/335
[51] Int. Cl.[2] .............. A61K 31/36
[58] Field of Search ............. 260/340.5; 424/282

[56] References Cited

UNITED STATES PATENTS

| | | | |
|---|---|---|---|
| 3,563,982 | 2/1971 | Bowers | 260/340.5 X |
| 3,637,752 | 1/1972 | Siddall | 260/340.5 |
| 3,829,577 | 8/1974 | Chodnekar et al. | 260/340.5 X |
| 3,941,879 | 3/1976 | Okauchi et al. | 424/282 X |

*Primary Examiner*—Ethel G. Love
*Attorney, Agent, or Firm*—Samuel L. Welt; Bernard S. Leon; William H. Epstein

[57] ABSTRACT

Alkyl or alkenyl ethers of 1,2-methylene dioxy benzene which are useful in combatting insects by interfering with their hormonal system.

17 Claims, No Drawings

METHYLENE DIOXYPHENYL ETHERS

SUMMARY OF THE INVENTION

In accordance with this invention, it has been found that phenyl derivatives of the formula:

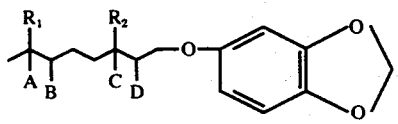
(I)

wherein $R_1$ is propyl, butyl or isobutyl; $R_2$ is methyl or ethyl group; A and B taken together form a carbon to carbon bond or an oxygen bridge; and C and D individually are hydrogen or taken together form a carbon to carbon bond;

are useful in combatting insects by upsetting their hormonal balance.

According to the process provided by the present invention, the phenyl derivatives of formula I hereinbefore are manufactured by:

a. reacting a compound of the general formula:

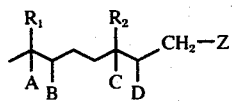
(II)

wherein $R_1$, $R_2$, A, B, C and D are as above; and Z is chlorine, bromine, iodine, tosyloxy or mesuloxy;

with a phenolate of the general formula:

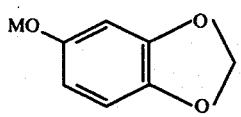
(III)

wherein M is an alkali metal or alkaline earth metal, or b. hydrogenating a phenyl derivative of formula I in which A and B taken together form an oxygen bridge and C and D taken together form a carbon to carbon bond, or c. epoxidizing a phenyl derivative of formula I in which A and B taken together form a carbon to carbon bond.

DETAILED DESCRIPTION

Preferred phenyl derivatives of formula I are those in which A and B taken together form an oxygen bridge. Also preferred are phenyl derivatives of formula I in which $R_2$ is methyl.

The novel compounds of formula I are compounds of the formula:

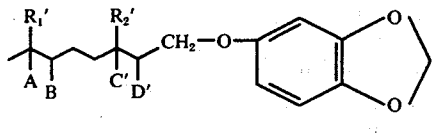
I-A wherein
$R_1'$ is propyl, n-butyl or isobutyl;
$R_2'$ is methyl or ethyl; A and B are as above;
C' and
D' are individually hydrogen or taken together form a carbon to carbon bond;
with the proviso that when $R_1'$ is isobutyl and $R_2'$ is methyl;
C' and D' are both hydrogen.

Among the preferred compounds of formula I-A are the following:
A compound of the formula:

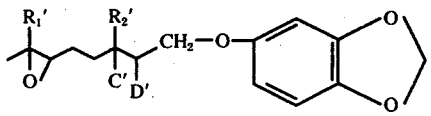
I-Ai wherein
$R_1'$, $R_2'$, C' and D' are as above;
with the proviso that when $R_1'$ is isobutyl and $R_2'$ is methyl;
C' and D' are both hydrogen;
and a compound of the formula:

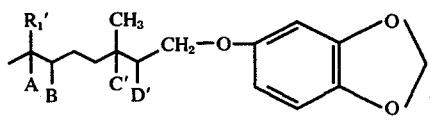
I-Aii wherein
$R_1'$, A, B, C' and D' are as above;
with the proviso that when $R_1'$ is isobutyl, C' and D' are both hydrogen.

Another group of preferred compounds of formula I-A are compounds of the formula:

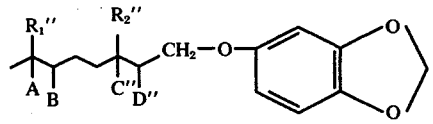
I-B wherein
A and B are as above;
$R_1''$ is propyl, or isobutyl;
$R_2''$ is methyl or ethyl;
C'' and D'' are individually hydrogen or taken together form a carbon to carbon bond; with the proviso that when $R_1''$ is isobutyl;
and $R_2''$ is methyl;
C'' and D'' are both hydrogen.

Among the preferred compounds of formula I-B are:
A compound of the formula:

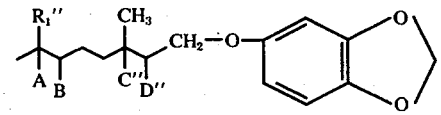
I-Bi wherein
$R_1''$, A, B, C'' and D'' are as above;
with the proviso that when $R_1''$ is isobutyl;
C'' and D' are both hydrogen and
A compound of the formula:

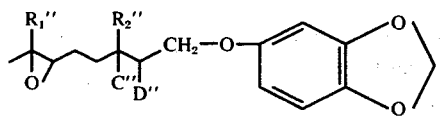

wherein $R_1''$, $R_2''$, $C''$ and $D''$ are as above; and with the proviso that when $R_1''$ is isobutyl and $R_2''$ is methyl; C and D are both hydrogen.

Particularly preferred compounds of formula I are:

4-[(6,7-epoxy-3,7-dimethyl-2-decenyl)-oxy]-1,2-(methylenedioxy)-benzene;

4-(6,7-epoxy-3,7-dimethyldecyl)-oxy]-1,2-(methylenedioxy)-benzene;

4-(6,7-epoxy-3-ethyl-7-methyl-2-decenyl)-oxy]-1,2-(methylenedioxy)-benzene;

4-[(6,7-epoxy-3-ethyl-7-methyldecyl)-oxy]-1,2-(methylenedioxy)-benzene;

4-[(6,7-epoxy-3,7,9-trimethyl-2-decenyl)-oxy]-1,2-(methylenedioxy)-benzene;

4-[(6,7-epoxy-3,7,9-trimethyldecyl)-oxy]-1,2-(methylenedioxy)-benzene;

4-[(6,7-epoxy-3-ethyl-7,9-dimethyl-2-decenyl)-oxy]-1,2-(methylenedioxy)-benzene;

4-[(6,7-epoxy-3-ethyl-7,9-dimethyldecyl)-oxy]-1,2-(methylenedioxy)-benzene;

4-[(6,7-epoxy-3,7-dimethyl-2-undecenyl)-oxy]-1,2-(methylenedioxy)-benzene;

4-[(6,7-epoxy-3,7-dimethylundecyl)-oxy]-1,2-(methylenedioxy)-benzene;

4-(6,7-epoxy-3-ethyl-7-methyl-2-undecenyl)-oxy]-1,2-(methylenedioxy)-benzene; and 4-[(6,7-epoxy-3-ethyl-7-methylundecyl)-oxy]-1,2-(methylenedioxy)-benzene.

Preferred starting materials of formuls II hereinbefore are:

1-bromo-3,7-dimethyl-2,6-decadiene;
1-bromo-3-ethyl-7-methyl-2,6-decadiene;
1-bromo-3,7,9-trimethyl-2,6-decadiene;
1-bromo-3-ethyl-7,9-dimethyl-2,6-decadiene;
1-tosyloxy-3,7-dimethyl-6-decene;
1-tosyloxy-3-ethyl-7-methyl-6-decene;
1-tosyloxy-3,7,9-trimethyl-6-decene;
1-tosyloxy-3-ethyl-7,9-dimethyl-6-decene; and
1-bromo-3,7-dimethyl-2,6-undecadiene.

The reaction of a halide, tosylate or mesylate of formula II with a phenolate of formula III in accordance with embodiment (a) of the present process is carried out in an inert organic solvent, preferably in dimethylformamide, dioxane, hexamethylphosphoric acid triamine, tetrahydrofuran, dimethyoxyethane or in a combination of two or more of these solvents. The reaction is expediently carried out using the phenol corresponding to the phenolate of formula III in the presence of an alkali metal or alkaline earth metal, a corresponding hydride or amide or an alkali metal hydroxide. By this means, the corresponding phenolate is formed from the phenol. Preferred alkali metals are sodium and potassium and preferred alkaline earth metals are calcium and magnesium. The temperature at which the reaction is carried out is of no particular significance. The reaction can be carried out expediently at a temperature between −20° C. and the boiling point of the reaction mixture. It is preferred to carry out the reaction at room temperature (from 15° to 25° C.) especially when Z in a starting material of fromula II represents a bromine atom.

Phenyl derivatives of formula I in which A and B together represent an oxygen bridge and C and D together represent an additional bond can be hydrogenated in accordance with embodiment b) of the present process using catalytically activated hydrogen in an inert organic solvent (e.g. ethyl acetate or methanol) at a temperaure between room temperature and the boiling point of the solvent and at normal or elevated pressure. Suitable catalysts are, for example, Raney nickel and noble metals such as platinum and palladium.

The epoxidation of phenyl derivatives of formula I in which A and B together represent an additional bond in accordance with embodiment (c) of the present process is expediently carried out by dissolving such a phenyl derivative in an inert solvent, especially in a halogenated hydrocarbon such as methylene chloride or chloroform, and treating the solution obtained with an organic peracide (e.g. perbenzoic acid, m-chloroperbenzoic acid or perphthalic acid) at a temperature range between 0° C. and room temperature (15° to 25° C.) or by suspending such a phenyl derivative in water, treating the suspension with a sufficient amount of an inert solvent (e.g. dioxane, tetrahydrofuran or 1,2-dimethoxyethane) to provide a homogeneous, concentrated solution and introducing N-bromosuccinimide portionwise into this solution at a temperature between 0° C. and room temperature (15° to 25° C.). The resulting bromohydrin can be converted smoothly into the desired epoxide by the action of alkalis, especially sodium methylate in methanol.

Certain of the starting materials of formula II hereinabove are novel. They can be prepared in the manner illustrated in the following formula scheme by, for example, reacting a compound of formula IV with acetylene in the presence of sodium amide in liquid ammonia and partially hydrogenating the resulting acetylenic compound of formula V with the aid of a partially deactivated catalyst (e.g. a lead/palladium catalyst deactivated with quinoline). The resulting alcohol of formula VI is halogenated, with allylic rearrangement, in a known manner. A phosphorus halide, especially phosphorus tribromide, is preferably used as the halogenating agent. The halogenating agent is reacted with an alcohol of formula VI in the cold, advantageously at a temperature between −10° and +5° C. Alternatively, a compound of formula IV can be converted in a known manner under the conditions of a Horner reaction into a compound of formula VII. Moreover, an acetylenic compound of formula V can be converted in a known manner under the condition of the citral synthesis of Saucy et al. [Helv. Chim. Acta 42, 1954 (1959)]into an alpha, beta-unsaturated aldehyde of formula VIII which, in turn, can be converted into a compound of formula IX by catalytic hydrogenation in methanol in the presence of Raney nickel with addition of sodium carbonate. The further conversion into the compounds of formulae IIa, IIb and IIc illustrated in the following formula scheme is likewise known per se.

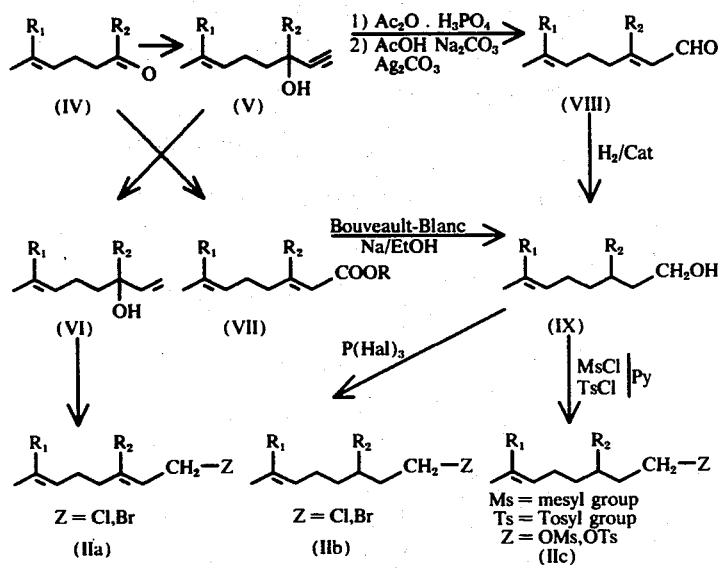

The compounds of formula IV hereinbefore can be prepared, for example, by the "acetoacetic acid synthesis" or by using acyl-malonic esters according to Hoffmann et al. [Liebigs Ann. Chem. 729, 52 (1969)] according to the following formula scheme; the conditions for carrying out the individual steps being known and conventional in the art.

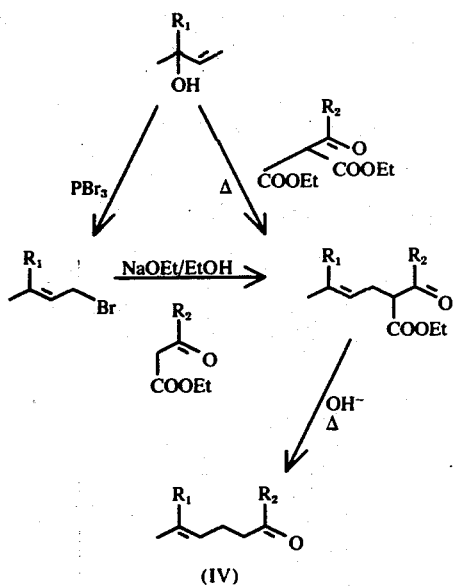

Insofar as the side-chain is unsaturated, the phenyl derivatives of formula I occur as cis/trans isomer mixtures. The isomer mixture can be separated into the individual isomers in the usual manner; for example, by fractional distillation or preparative gas chromatography. Further, the starting materials of formula II, insofar as they are present as an isomer mixture, can also be separated into the individual isomers in the usual manner; for example, by fractional distillation or chromatography.

The phenyl derivatives of formula I belong to a known class of insect growth regulators which invade the hormonal system of the insect's organism and disturb the transformation to the imago, the laying of viable eggs and the development of laid normal eggs. The animals are indirectly killed and the sequence of generations is interrupted. The phenyl derivatives of formula I are almost non-poisonous to vertebrates. The toxicity of the phenyl derivatives of formula I lies at over 1000 mg/kg body weight. Moreover, they are readily degraded and thus the risk of a cumulation is excluded. They may accordingly be used for the control of pests in animals, plants and provisions.

In accordance with the present invention, it has surprisingly been found that the phenyl derivatives of formula I possess an extraordinary high activity against insects from the orders Lepidoptera and Coleptera. They can be used, in particular, for combatting phytophagic Lepidoptera and Coleptera, especially in the later states. Thus, for example, 4-[(6,7-expoy-3,7,9-trimethyl-2-decenyl)-oxy]-1,2-(methylenedioxy)benzene and 4-[(6,7-epoxy-3,7-dimethyl-2-decenyl)-oxy]-1,2(methylenedioxy)benzene in the test against the last larval state of Adoxophyes orana in a dosage of $10^{-9}$ g/cm$^2$ and 4-[(6,7-epoxy-3,7,9-trimethyldecyl)-oxy]-1,2-(methylenedioxy)-benzene in the test against the last larval state of Letinotarsa decemlineata in a spraywash concentration of 0.001% each shown an activity of 100%.

Further pests against which the phenyl derivative of formula I show a good activity are:

| | |
|---|---|
| Agrotis spp. | (cut worms) |
| Alabama argillacea | (cotton lead worm) |
| Argyrotaenia spp. | |
| Autographa californica | (alfalfa looper) |
| Anthonomus grandis | (boll weevil) |
| Bucculatrix thurberiella | (cotton leaf perforator) |
| Carpocapsa pomonella | (codling moth) |
| Chilo suppressalis | (Asiatic rice borer) |
| Choristoneura spp. | |
| Diatraea spp. | |
| Epilachna varivestis | (Mexican bean beetle) |
| Grapholita spp. | |
| Heliothis spp. | |
| Hypera spp. | |
| Lambdina spp. | |
| Lissorhoptrus oryzophilus | (rice water weevil) |
| Ostrinia nubilalis | (European corn borer) |
| Pectinophora gossypiella | (Pink bollworm) |
| Pieris spp. | |
| Platynota stultana | (omnivorous leaf roller) |

| | |
|---|---|
| Porthetria dispar | (gypsy moth) |
| Spodoptera spp. | |
| Trichoplusia ni | (cabbage looper) |
| Zeiraphera diniana | (Larch tortrix moth) |

The phenyl derivatives of formula I can be used as pesticides in the form of concentrates, granulates or, together with carriers, in the form of sprays, aerosols or powders. In accordance with this invention, any conventional inert carrier material utilized in forming insecticides and juvenile hormone compositions can be utilized in preparing the compositions containing the compound of formula I or mixtures thereof for use in combatting insect pests. For certain purposes, it can be advantageous to use emulsions, suspensions or solution which contain emulsifiers or wetting agents. Examples of carrier materials include chalf, talc, bentonite, kaolin, diatomeceous earth, siliceous earth, fuller's earth, lime, gypsum, powders and dusts from organic waste products, polymers such as polyvinyl chloride, polyethylene, polyacrylate, polystrene and mixed polymerizates etc. The pesticidal compounds can also contain additives such as, for example, antioxidants, UV-absorbers and other stabilizers as well as aromas and attractants etc. The pesticidal compositions can also be provided in forms which release the active ingredient in dosed amount such as, for example, microcapsules, coated granulates, solutions in polymeric materials etc. It will be appreciated that the foregoing examples are only given by way of illustration and are not intended to limit the invention in any respect.

In general, the pesticidal compositions provided by the present invention can be formulated according to the procedures described, for example, in Farm Chemicals, Volume 128, page 52 and subsequent pages. The pesticidal compositions can also contain other additives such as emulsifiers or masking agents.

The pesticidal compositions provided by this invention can be made up in the form of concentrates which are suitable for storage and transport. Such concentrates can contain, for example, 40–90% of a phenyl derivative of formula I. These concentrates can be diluted with the same or different carrier materials to provide concentrations which are suitable for practical use. In the ready-for-use pesticidal composition in the form of a spray concentrations of 0.005–0.5%, preferably 0.1% of a phenyl derivative of formula I can, for example, be present. The concentration can, however, also be smaller or larger.

Generally, in controlling pests such as Lepidoptera and Coleoptera, the compounds of formula I above thereof are applied such as by spray to the plants, etc. in an amount of 0.05 to 5 kg/ha. Generally, it is preferred to utilize the compounds of formula I above in a composition with a suitable inert carrier. Any conventional inert carrier can be utilized.

The pesticidal composition provided by the present invention can be used against pests according to the customary methods; for example, by contact or by intake with the food. It will be appreciated from the foregoing that the invention includes within its scope:

a. a pesticidal composition for control of Lepidoptera and Coleoptera which contains as an essential active ingredient or essential active ingredients one or more of the phenyl derivatives of formula I hereinbefore in association with a compatible carrier material; and b. a method of rendering a locus subject to or subjected to attack by Lepidoptera and Coleoptera free from such attack by applying to said locus a pesticidal composition as hereinbefore defined or one or more of the phenyl derivatives of formual I hereinbefore.

The phenyl derivatives for formual I are novel subject to the proviso that when $R_1$ represents the isobutyl group and $R_2$ represents the methyl group then C and D each represent a hydrogen atom. These novel phenyl derivatives are also included within the scope of the present invention.

The following examples are illustrative but not limitative of the invention. In the examples, the ether utilized was diethyl ether and the temperature is in degrees centigrade (°C.). The term 80% m-chloroperbenzoic acid designates a minimum content of 80% by weight m-chloroperbenzoic acid. The term soda designates sodium carbonate. The term dilute sulfuric acid denotes an aqueous solution containing 10% by weight sulfuric acid. The term concentrated hydrocloric acid denotes an aqueous solution containing 32% by weight hydrogen chloride.

EXAMPLE 1

13.8 g. of sesamol and 40 ml. of N,N-dimethylformamide are treated, while stirring at 0°–5° C. and within a few minutes, with 5.6 g. of freshly powdered potassium hydroxide. The ice-bath is then removed and the mixture is left to stir at room temperature for 4–5 hours. The mixture is cooled again and treated dropwise at 1°–3° C. with a solution of 25.9 g. of 1-bromo-3,7,9-trimethyl-2,6-decadiene in 10 ml. of N,N-dimethylformamide over a period of one hour. Subsequently, the mixture is left to stir at room temperature for 24 hours. For the working-up, the mixture is poured into 150 ml. of ice-water and extracted with two 100 ml. portions of hexane. The extracts are washed successively with two 50 ml. portions of 10% by weight aqueous sodium hydroxide, two 50 ml. portions of water and 50 ml. of saturated aqueous sodium chloride solution, then dried over sodium sulfate and evaporated. By chromatgraphy on silica gel with hexane/ether (19:1 parts by volume) there is obtained pure 1,2-(methylenedioxy)-4-[(3,7,9-trimethyl-2,6-decadienyl)-oxy]-benzene of boiling point (bulb tube) 145° C./0.035 mm Hg; $n_D^{22} = 1.5206$.

EXAMPLE 2

19.8 g. of 3,7,9-trimethyl-1,6-decadien-3-ol, 100 ml. of hexane and 1 ml. of pyridine and cooled to −15° C. and treated dropwise over a period of 1.5 hours with a solution of 4 ml. of phosphorus tribromide in 50 ml. of hexane while maintaining the temperature between −15° and −10° C. The mixture is stirred for a further 90 minutes while slowly warming to room temperature. For the working-up, the mixture is poured on to 50 ml. of ice-water, the organic phase is separated and washed once with 20 ml. of 10% soda solution, once with 50 ml. of semi-saturated aqueous sodium chloride solution and once with 50 ml. saturated sodium chloride solution, dried over sodium sulphate and evaporated under reduced pressure. There is obtained 1-bromo-3,7,9-trimethyl-2,6-decadiene.

EXAMPLE 3

To 10 g. of 1,2-(methylenedioxy)-4-[(3,7,9-trimethyl-2,6-decadienyl)oxy]-benzene dissolved in 100 ml. of methylene chloride are added portionwise, while stirring and cooling with ice at 1°–5° C., 6.85 g. of 80% m-chloroperbenzoic acid and the mixture is stirred for a further 2 hours while cooling with ice. The mixture is subsequently diluted with 200 ml. of ether and washed successively with ice-cold 1-N aqueous sodium hydroxide, water and saturated aqueous sodium chloride solution, dried over sodium sulphate and evaporated. By chromatography on silica gel with hexane/ether (4:1 parts by volume), there is obtained pure 4-[(6,7-epoxy-3,7,9-trimethyl-2-decenyl)-oxy]-1,2-(methylenedioxy)-benzene of boiling point (bulb tube) 135°–140° C./0.02 mm Hg.; $n_D^{22} = 1.5168$.

EXAMPLE 4

1.66 g. of 4-[(6,7-epoxy-3,7,9-trimethyl-2-decenyl)-oxy]-1,2-(methylenedioxy)-benzene are dissolved in 30 ml. of ethyl acetate and hydrogenated by passing hydrogen gas in the presence of 50 mg. of platinum oxide until uptake of the theoretical amount of hydrogen. The catalyst is then filtered off and the filtrate evaporated. By chromatography on slica gel in hexane/ether (9:1 parts by volume) there is obtained pure 4-[(6,7-epoxy-3,7,9-trimethyldecyl)-oxy]-1,2-(methylenedioxy)-benzene of boiling point (bulb tube) 128° C./0.03 mm Hg; $n_D^{23} = 1.5027$.

EXAMPLE 5

3.45 g. of sesamol in 25 ml. of N,N-dimethylformamide and treated, while cooling with ice, with 1.55 g. of freshly powdered potassium hydroxide. The ice-bath is then removed and the mixture is left to stir at room temperature for 2 hours. A solution of 8.8 g. of 1-tosyloxy-3,7,9-trimethyl-6-decene in 5 ml. of N,N-dimethylformamide is then allowed to drop in at 0°–5° C. over a period of 30 minutes. After stirring for a further 2 hours at room temperature, the mixture is poured on to 100 ml. of ice-water and extracted with two 100 ml. portions of hexane. The extracts are washed successively with 10% by weight aqueous sodium hydroxide, water and saturated aqueous sodium chloride solution, dried over sodium sulphate and evaporated. By chromatography on silica gel with hexane/ethyl acetate (98:2 parts by volume) there is obtained pure 1,2-(methylenedioxy)-4-[(3,7,9-trimethyl-6-decenyl)-oxy]-benzene of boiling point (bulb tube) 125° C./0.01 mm Hg.

EXAMPLE 6

5 g. of Raney nickel are suspended in 200 ml. of methanol and treated slowly with a solution of 2.5 g. of soda in 5 ml. of water. To this mixture are added 97 g. of 3,7,9-trimethyl-2,6-decadien-1-al dissolved in 0.8 liters of methanol and the resulting mixture is hydrogenated. After uptake 2 of equivalents of hydrogen, the catalyst is filtered off, rinsed with 50 ml. of methanol and the filtrate evaporated. The residue is taken up in 300 ml. of ether, washed three times with 200 ml. of water each time, dried over sodium sulphate and evaporated. By distillation there is obtained pure 3,7,9-trimethyl-6-decen-1-ol of boiling point 90° C/0.7 mm. Hg; $n_D^{25} = 1.4570$.

EXAMPLE 7

79.5 g. of 3,7,9-trimethyl-6-decen-1-ol and 75 ml. of pyridine are treated portionwise with 76 g. of toluene-4-sulphonic acid chloride while cooling with ice and stirring. The thus-obtained thick, cream-colored mass is then stirred for a further 5 hours at 0°–5° C. For the working-up, the mixture is poured on to 420 ml. of ice-water and 140 ml. of concentrated aqueous hydrochloric acid and extracted twice with 300 ml. of ether each time. The extracts are washed twice with water, then with semisaturated aqueous sodium chloride solution and finally with saturated sodium chloride solution dried over sodium sulphate/potassium carbonate and evaporated. There is obtained 1-tosyloxy-3,7,9-trimethyl-6-decene.

EXAMPLE 8

By the procedure of Example 1, 1-bromo-3,7-dimethyl-2,6-decadien is reacted with sesamol to obtain 4-[(3,7-dimethyl-2,6-decadienyl)-oxy]-1,2-(methylenedioxy)-benzene of boiling point (bulb tube) 140° C./0.025 mm Hg.; $n_D^{23} = 1.5237$.

EXAMPLE 9

By the procedure of Example 2, 3,7-dimethyl-1,6-decadien-3-ol and phosphorus tribromide is converted to 1-bromo-3,7-dimethyl-2,6-decadiene.

EXAMPLE 10

By the procedure of Example 1, 1-bromo-3-ethyl-7,9-dimethyl-2,6-decadiene is reacted with sesamol to obtain 1,2-(methylenedioxy-4-[(3-ethyl-7,9-dimethyl-2,6-decadienyl)-oxy]-benzene; $n_D^{24} = 1.5190$.

EXAMPLE 11

162.2 g. of diethyl-propionyl malonate are heated to 165° C. and treated dropwise over a period of 4 hours with 64.1 g. of 3,5-dimethyl-1-hexen-3-ol while stirring. The alcohol formed is continuously distilled off and the carbon dioxide evolution, which beings immediately, is recorded. After completion of the addition, the mixture is heated to 190°–195° C. (internal temperature) within 15 minutes and maintained at this temperature until carbon dioxide evolution is no longer detectable (ca 2 hours). The cooled mixture is subsequently treated with 250 ml. of 20% by weight aqueous sodium hydroxide and 50 ml. of ethanol and heated to reflux for 2 hours. For the working-up, the mixture is acidified at ca 40° C. with 190 ml. of 10-N aqueous sulphuric acid and extracted with two 500 ml. portions of ether. The extracts are washed with two 300 ml. portions of 10% by weight aqueous sodium bicarbonate solution and with 300 ml. of saturated sodium chloride solution, dried over sodium sulphate and freed from solvent on a rotary evaporator. The residue is distilled over a short Vigreaux column. There is obtained pure 7,9-dimethyl-6-decen-3-one of boiling point 105° –107° C./8 mm Hg.; $n_D^{24} = 1.4470$.

EXAMPLE 12

To a Grignard solution, prepared from 12.5 g. of magnesium and 57.8 g. of vinyl bromide in 130 ml. of tetrahydrofuran, is slowly added dropwise at 0°–5° C. a solution of 40.11 g. of 7,9-dimethyl-6-decen-3-one in 90 ml. of tetrahydrofuran. The mixture is left to stir for 2 hours at room temperature, then poured on to 300 ml. of ice-water, acidified with dilute sulphuric acid and extracted three times with ether. The extracts are washed with 10% by weight aqueous sodium bicarbonate solution and saturated sodium chloride solution, dried over sodium sulphate and evaporated. By distillation there is obtained pure 3-ethyl-7,9-dimethyl-1,6-decadien-3-ol; $n_D^{24} = 1.4631$; boiling point - 71° C./0.65 mm Hg.

EXAMPLE 13

By the procedure described in Example 2, 33.65 g. of 3-ethyl-7,9-dimethyl-1,6-decadien-3-ol and 6.6 ml. of phosphorus tribromide are reacted to produce 1-bromo-3-ethyl-7,9-dimethyl-2,6-decadiene.

EXAMPLE 14

By the procedure described in Example 3; from 4-[(3,7-dimethyl-2,6-decadienyl)-oxy]-1,2-(methylenedioxy)-benzene there is obtained 4-[(6,7-epoxy-3,7-decenyl)-oxy]-1,2-(methylenedioxy)-benzene; $n_D^{23} = 1.5192$; and from 4-[(3-ethyl-7,9-dimethyl-2,6-decadienyl)-oxyl]-1,2-(methylenedioxy)-benzene there is obtained 4-[(6,7-epoxy-3-ethyl-7,9-dimethyl-2-decenyl)-oxy]-1,2-(methylenedioxy)-benzene; $d_D^{25} = 1.51413$.

EXAMPLE 15

By the procedure described in Example 4:
from 4-[(6,7-epoxy-3,7-dimethyl-2)-oxy]-1,2-(methylenedioxy)benzene there is obtained there is obtained 4-[(6,7-epoxy-3,7-dimethyl-decyl)-oxy]-1,2-(methylenedioxy)-benzene of boiling point (bulb tube) 150° C./0.03 mm Hg; $n_D^{25} = 1.5048$; and from 4-[(6,7-epoxy-3-ethyl-7,9-dimethyl-2-decenyl)-oxyl-1,2-(methylenedioxy)-benzene there is obtained 4-[(6-epoxy-3-ethyl-7,9-dimethyldecyloxyl]-1,2-(methylenedioxy)-benzene; $n_D^{24} = 1.5005$.

EXAMPLE 16

By the procedure described in Example 1, 1-bromo-3,7-dimethyl-2,6-undecadiene is reacted with sesamol to produce 4-[(3,7-dimethyl-2,6-undecadienyl)-oxy]-1,2-(methylenedioxy)-benzenel $n_D^{25} = 1.5220$.

EXAMPLE 17

By the procedure described in Example 13, from 6-methyl-5-decen-2-one and vinyl-magnesium bromide there is obtained 3,7-dimethyl-1,6-undecadien-3-ol; $n_D^{26} = 1.4618$, boiling point 116° C./9 mm Hg. This alcohol is reacted with phosphorus tribromide by the procedure of Example 13 to give 1-bromo-3,7-dimethyl-2,6-undecadiene.

EXAMPLE 18

By the procedure described in Example 3, from 4-[(3,7-dimethyl-2,6-undecadienyl)-oxy]-1,2-(methylenedioxy)-benzene there is obtained 4-[(6,7-epoxy-3,7-dimethyl-2-undecenyl)-oxy]-1,2-(methylenedioxy)-benzene; $n_D^{25} = 1.5164$.

EXAMPLE 19

By the procedure described in Example 4, from 4-[(6,7-epoxy-3,7-dimethyl-2-undecenyl)-oxy]-1,2-(methylenedioxy)-benzene there is obtained 4-[(6,7-epoxy-3,7-dimethyl-undecyl)-oxy]-1,2-(methylenedioxy)-benzene; $n_D^{25} = 1.5019$.

We claim:
1. A phenyl derivative having the formula:

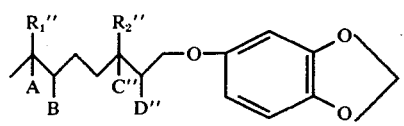

(I)

wherein
$R_1''$ is propyl, butyl or isobutyl;
$R_2''$ is methyl, A and B taken together form an oxygen and C'' and D'' are individually hydrogen or taken together form a carbon to carbon bond; with the provision that when $R_1''$ is isobutyl and $R_2''$ is methyl, C'' and D'' both are hydrogen.

2. A compound of claim 1 wherein said compound has the formula:

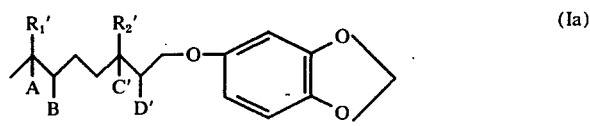

(Ia)

wherein
$R'_1$ is propyl or isobutyl group,
$R_2$ is methyl;
A and B taken together form an oxygen bridge;
and C' and D' individually are hydrogen or taken together form a carbon to carbon bond, with the provision that when $R'_1$ is isobutyl and $R_2'$ is methyl;
C' and D' are both hydrogen atoms.

3. The compound of claim 1 wherein $R_1''$ is propyl.
4. The compound of claim 1 wherein said compound is 4-[(6,7-Epoxy-3,7-dimethyl-2-decenyl)-oxy]-1,2-(methylenedioxy)-benzene.
5. The compound of claim 4 wherein said compound is 4-[(6,7-Epoxy-3,7-dimethyldecyl)-oxy]-1,2-(methylenedioxy)-benzene.
6. The compound of claim 1 wherein $R_1''$ is isobutyl.
7. The compound of claim 6 wherein said compound is 4-[(6,7-Epoxy-3,7,9-trimethyldecyl)-oxy]-1,2-(methylenedioxy)-benzene.
8. The compound of claim 1 wherein said $R_1''$ is n-butyl.
9. The compound of claim 8 wherein said compound is 4-[(6,7-Epoxy-3,7-dimethyl-2-undecenyl)-oxy]-1,2(methylenedioxy)-benzene.
10. The compound of claim 8 wherein said compound is 4-[(6,7-Epoxy-3,7-dimethylundecyl)-oxy]-1,2-(methylenedioxy)-benzene.
11. A pesticidal composition for th control of Lepidoptera and Coleoptera which contains as an essential active ingredient or essential active ingredients one or more of the phenyl derivatives of the formula:

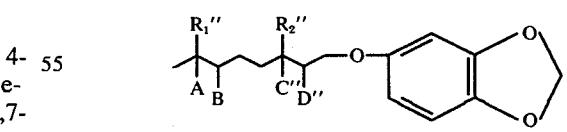

wherein
$R_1''$ is propyl, butyl or isobutyl;
$R_2''$ is methyl; A and B taken together form an oxygen bridge
and C'' and D'' are individually hydrogen or taken together form a carbon to carbon bond.
12. The pesticidal composition of claim 11 wherein said phenyl derivative is 4-[(6,7-epoxy-3,7-dimethyl-2-decenyl)-oxy]-1,2-(methylenedioxy)-benzene.

13. A pesticidal composition of claim 11 wherein said phenyl derivative is 4-[(6,7-epoxy-3,7-dimethyldecyl)-oxy]-1,2-(methylendioxy)-benzene.

14. A pesticial composition of claim 11 wherein said phenyl derivative is 4-[(6,7-epoxy-3,7,9-trimethyl-2-decenyl)-oxy]-1,2-(methylenedioxy)-benzene.

15. A pesticial composition of claim 11 wherein said phenyl derivative is 4-[(6,7-epoxy-3,7,9-trmethyl-decyl)-oxy]-1,2-(methylenedioxy)-benzene.

16. A process for protecting materials from Lepidoptera and Coleoptera comprising applying to said material an effective amount of a composition containing as an active ingredient a compound of the formula:

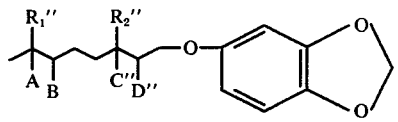

wherein
$R_1''$ is ;propyl, butyl or isobutyl;
$R_2''$ is methyl, A and B taken together form an oxygen bridge and
$C''$ and $D''$ are individually hydrogen or taken together form a carbon to carbon bond;

or mixtures thereof and an inert carrier.

17. The process of claim 16 wherein said material is a foodstuff, feed, textile or plant.

* * * * *